(12) United States Patent
Webb

(10) Patent No.: US 10,016,379 B2
(45) Date of Patent: Jul. 10, 2018

(54) METHOD OF TREATMENT FOR THIRD SPACING

(71) Applicant: Robin L. Webb, Holland, MI (US)

(72) Inventor: Robin L. Webb, Holland, MI (US)

( * ) Notice: Subject to any disclaimer, the term of this patent is extended or adjusted under 35 U.S.C. 154(b) by 0 days.

(21) Appl. No.: 15/066,258

(22) Filed: Mar. 10, 2016

(65) Prior Publication Data

US 2017/0119709 A1 May 4, 2017

Related U.S. Application Data

(60) Provisional application No. 62/248,518, filed on Oct. 30, 2015.

(51) Int. Cl.
*A61K 31/19* (2006.01)
*A61K 31/192* (2006.01)

(52) U.S. Cl.
CPC .................................. *A61K 31/192* (2013.01)

(58) Field of Classification Search
CPC .............................. A61K 31/192; A61K 31/19
See application file for complete search history.

(56) References Cited

U.S. PATENT DOCUMENTS

| 4,757,089 A | 7/1988 | Epstein |
| 5,686,100 A | 11/1997 | Wille et al. |
| 2007/0142473 A1 | 6/2007 | Solomon et al. |
| 2011/0003747 A1 | 1/2011 | Coloumbe et al. |
| 2012/0053156 A1* | 3/2012 | Mathiowitz .......... C07D 277/42 514/158 |

FOREIGN PATENT DOCUMENTS

| DE | 10004651 A1 | 8/2001 |
| WO | 2012059090 A1 | 5/2012 |

OTHER PUBLICATIONS

International Searching Authority, "Notification of Transmittal of the International Search Report and the Written Opinion of the International Searching Authority", for PCT/US2016/059013,dated Jan. 25, 2017, 8 pages.

Oh et al., "Loop Diuretics in Clinical Practice" Electrolyte Blood Press., vol. 13, No. 1, p. 17-21 (Jun. 30, 2015) p. 19-20.
Munar et al., "Acute Renal Disease" in Textbook of Therapeutics. Philadelphia: Lippincott Williams & Wilkins (2006) [online] [retrieved on Dec. 19, 2016]. Retrieved from the Internet <URL:https://books.google.com/books?id=aVmRWrknaWgC &printsec=frontcover#v=onepage&q&f=false>Ch 42, p. 1112, 1131.
Chaabane et al., "DRESS Syndrome: furosemide, another culprit drug" EAACI Online Library (Jun. 6, 2015) [online] [retrieved on Dec. 16, 2016]. Retrieved from the Internet <URL:http://eaaci.multileaming.com/eaaci/2015/barcelona/104580/amel.chaabane.dress.syndrome.furosemide.another.culprit.drug.html?f=p6m3e814o10445> p. 1.
American Pharmacists Association, "FDA approves ethacrynate sodium for injection" (Aug. 10, 2015) [online] (=[retrieved on Dec. 19, 2016]. Retrieved from the Internet <URL:https://www.pharmacist.com/fda-approves-ethacrynate-sodium-injection> p. 1.
Susan Simmons Holcomb, "Third-spacing: When body fluid shifts" Nursing 2009 Critical Care, vol. 4, No. 2 (Mar. 2009) [online] [retrieved on Dec. 15, 2016]. Retrieved from the Internet <URL:http://www.nursingcenter.com/journalarticle?Article_ID=859815>p. 9-10.
Josie Evans, "About Symptoms" (Sep. 1, 2015) [online] [retrieved on Dec. 19, 2016). Retrieved from the Internet <URL:http://web.archive.org/web/20150901094639/http://www.iamast.com/about-symptoms/4564711924> p. 2, 10.
Ben m'rad et al., "Drug-Induced Hypersensitivity Syndrome: Clinical and Biologic Disease Patterns in 24 Patients" Medicine, vol. 88, No. 3, p. 131-140 (May 2009) p. 131.
Yoo et al., "Drug Rash With Eosinophilia and Systemic Symptoms Syndrome Induced by Chloral Hydrate in Early Childhood" Allergy Asthma Immunol. Res., vol. 6, No. 3, p. 270-272 (May 2014) p. 270.
Aton Pharmacy, "Tablets Edecrin (Ethacrynic Acid) and Intravenous Sodium Edecrin (Ethacrynate Sodium)", PDR Sheet LB0089-00.indd Feb. 14, 2012, Nov. 2011, 3 pages.

* cited by examiner

*Primary Examiner* — Sudhakkar Katakam
(74) *Attorney, Agent, or Firm* — Zarley Law Firm, P.L.C.

(57) ABSTRACT

A method of treatment for third spacing is provided. The method includes identifying an adverse factor, which includes conditions causing an increase in vascular permeability resulting in third spacing. The method also includes diagnosing the patient with third spacing, which can include third spacing of fluids, materials, or both. The patient is treated with a therapeutically effective amount of a non-increased vascular permeability modifier loop diuretic, such as a non-sulfonamide loop diuretic like ethacrynic acid or ethacrynate sodium.

25 Claims, 5 Drawing Sheets

METHOD OF TREATMENT FOR THIRD SPACING

CROSS REFERENCE TO RELATED APPLICATION

This application claims the benefit to U.S. Application No. 62/248,518 filed Oct. 30, 2015, incorporated by reference herein.

BACKGROUND OF THE INVENTION

This invention is directed to a method of treatment of third spaced fluids, materials, or both. More particularly, this invention is directed to a method of treatment of third spaced fluids or materials, wherein a non-sulfonamide loop diuretic medicament is administered that addresses increased vascular permeability after identification of an adverse factor resulting in third spaced fluids or materials.

Sulfa/sulfonamide compounds in medicine are a diverse class of compounds having a sulfonamide group ($RSO_2NH_2$, where R is an organic group). Compounds having a sulfonamide group attached to them have been used for various medicinal uses in humans as well as animals. These compounds are most frequently used as antibiotics and diuretics in humans. Because of their ease of manufacture, cost, and widespread use, healthcare providers readily use them.

As with any medication, there are adverse considerations that have to be taken into consideration when using the sulfa/sulfonamide compounds. These adverse considerations may not be apparent to the patient, patient family, care givers, providers and manufactures of the various medications at the initial time of manufacture, consideration of treatment, initial treatment, or ongoing treatment. Recent evidence surrounding the use of sulfa/sulfonamide compounds indicates there is an association with Drug Induced Hypersensitivity Syndrome (DIHS) in some individuals.

Due to the association of DIHS with sulfa/sulfonamide compounds, ethacrynic acid, as well as ethacrynate sodium, has been used for quite some time as a loop diuretic with research beginning in the late 1950s. Although ethacrynic acid and ethacrynate sodium, which are non-sulfonamide based medicinal agents, have adverse reactions associated with them, they have not been associated with DIHS to the extent that the sulfa/sulfonamide compounds have.

Despite these advances, problems remain. Specifically, the art currently overlooks that there are many causative factors that contribute to increased vascular permeability, which causes third spacing, that are not due to hypersensitivity, but are the result of contributory factors or side effects associated with these sulfa/sulfonamide compounds. Furthermore, these contributory factors are not limited to sulfa/sulfonamide compounds as will be discussed elsewhere.

Similarly, the indications within the art currently for ethacrynic acid and ethacrynate sodium is limited in scope. More pointedly, current indications of the commercial formulations of ethacrynic acid and ethacrynate sodium are limited to various forms of treatment of edema, and thereby overlook indications for the treatment of third spacing of fluid or materials, which are resistant to known diuretics. These deficiencies in the art have resulted in the continued treatment of patients with medications that are unnecessary and potentially harmful to the overall wellbeing of the patient. As such, a need in the art exists to address these deficiencies.

Thus it is a primary objective of this invention to provide a method that improves upon the state of the art.

Another objective of this invention is to limit the number of medicaments a patient is exposed to.

Yet another objective of this invention is to provide a treatment that provides the possibility of cessation of treatment.

Another objective of this invention is to treat and remove the underlying offending agent.

Yet another objective of this invention is to provide an agent that does not contribute to the activation of agents that restore homeostasis, including bradykinin, complement cascade, histamine, and related mediators, in patients which in turn contribute to third spacing of fluid or materials.

These and other objectives, features, and advantages of the invention will become apparent from the specification and claims.

BRIEF SUMMARY OF THE INVENTION

The present invention is a method of treatment for third spacing. The method includes identifying an adverse factor, which includes conditions causing an increase in vascular permeability resulting in third spacing. Adverse factors can be allergies, hypersensitivities, adverse reactions, or can be the result of the human body's natural response to outside stimulus in attempt to maintain homeostasis, as well as other factors.

The method also includes diagnosing the patient with third spacing, which can include third spacing of fluids, materials, or both. Once diagnosed, the patient is then treated with a therapeutically effective amount of a non-increased vascular permeability modifier loop diuretic, such as a non-sulfonamide loop diuretic like ethacrynic acid or ethacrynate sodium. After being treated, the patient is monitored until the third spacing is resolved. Once resolved, treatment is stopped or continued for as short a time as possible using the lowest dose of medicinal agents.

DETAILED DESCRIPTION OF THE INVENTION

Figure 1:
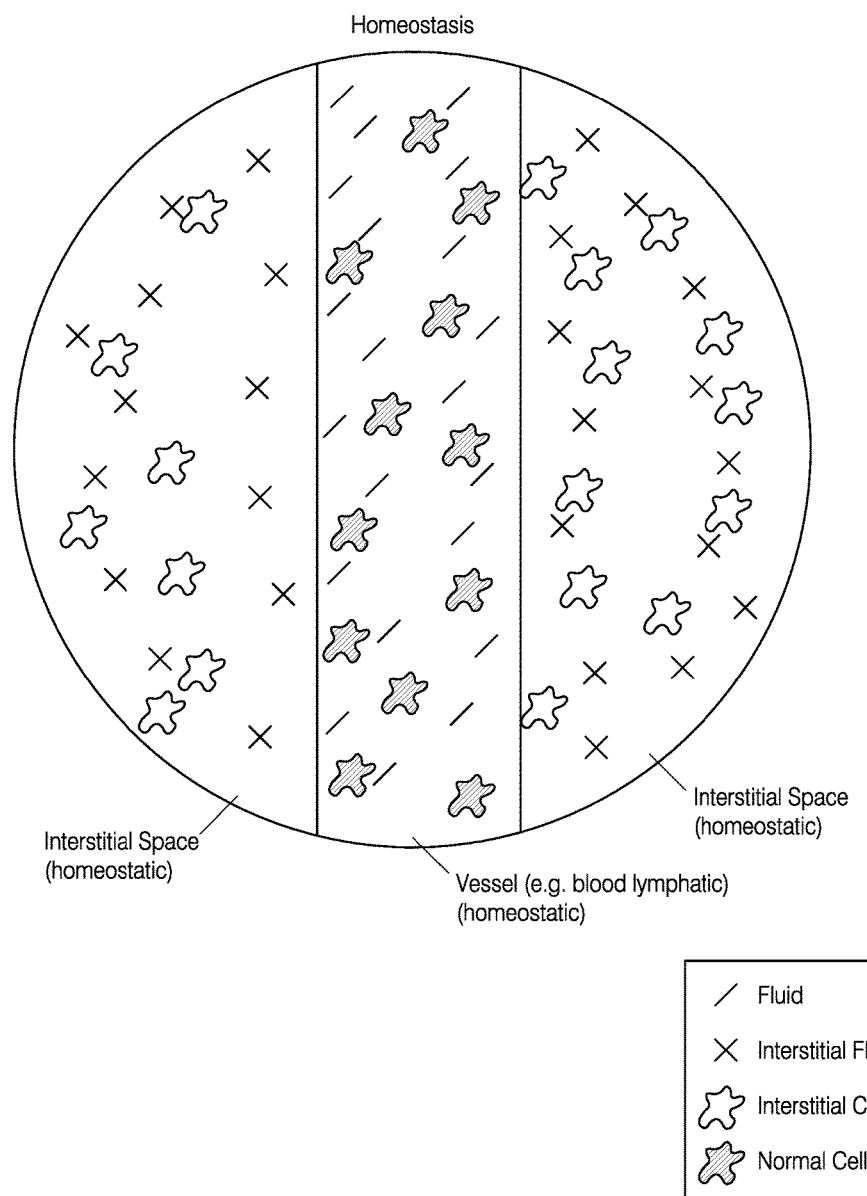
FIG. 1 is a side cross sectional view of a vessel and interstitial space and schematic of homeostasis.

Edema Versus Third Spacing of Fluid:

As depicted in FIG. 1, a homeostatic blood vessel is presented, which can be other vessels, such as a lymphatic vessel, that is intact. Under homeostatic conditions, the pressure in the vessel is maintained and so is the volume. The normal elements of the vessel, e.g. whole blood in a blood vessel along with small and large proteins like albumin, are also contained within the vessel. Through diffusion small molecules, such as water, small proteins, and glucose, can pass from the vessel into the surrounding interstitial space or be actively transported there via mechanisms associated with the cells lining the vessel. In this environment, the fluid in the vessel is in hydrostatic and oncotic pressure equilibrium with the interstitial space or region.

These two forces are greatly dependent on proteins, which are normally contained in the vessel (such as albumin) or in the interstitial regions as part of the normal adjacent tissue. Due to their size, these molecules do not move between compartments. For illustration, albumin would stay in a blood vessel instead of moving into the surrounding tissue. The larger the protein the more ions it can hold (the larger the oncotic value) and thus the more water follows. These hydrophilic or water loving complexes exert forces in the vessel and interstitial region, respectively, which oppose each other. They are responsible for much of the fluid retention in the body. Homeostasis occurs when pressures in the vessel and interstitial regions are in equilibrium but oppose each other.

Figure 2:
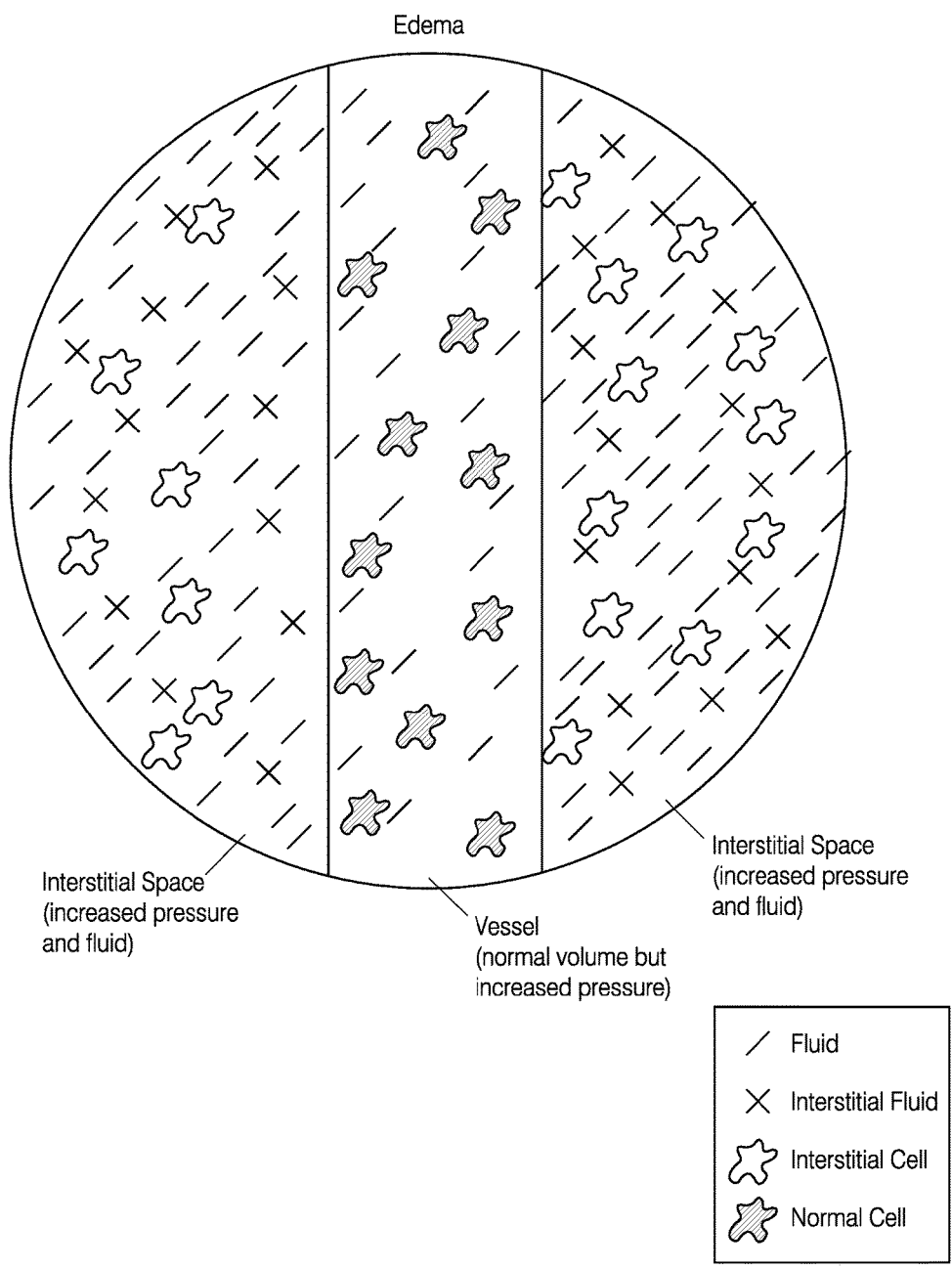
FIG. 2 is a side cross sectional view of a vessel and interstitial fluid and schematic of edema.

FIG. 2 depicts edema. Here, edema denotes an excess of fluid in the interstitial tissue or serous cavities that is either exudate, meaning, protein rich, or transudate, meaning, protein poor. Edema results from an increased pressure in the vessel. More specifically, increased hydrostatic pressure in the vessel results in disruption of the homeostasis described above thereby forcing fluid into the interstitial region adjacent to it. The integrity of the vessel is maintained and there is very little leakage of larger molecules, such as albumin and other normal components of the vessel, into the surrounding tissue. As such, the body accumulates more fluid due to it being forced out of the vessel by hydrostatic pressure, but not oncotic pressure. Edema is something that most individuals can visually appreciate as swelling of a peripheral region of the body. On average it take 3.3 liters—almost seven pounds—or more to be clinically apparent.

Figure 3:
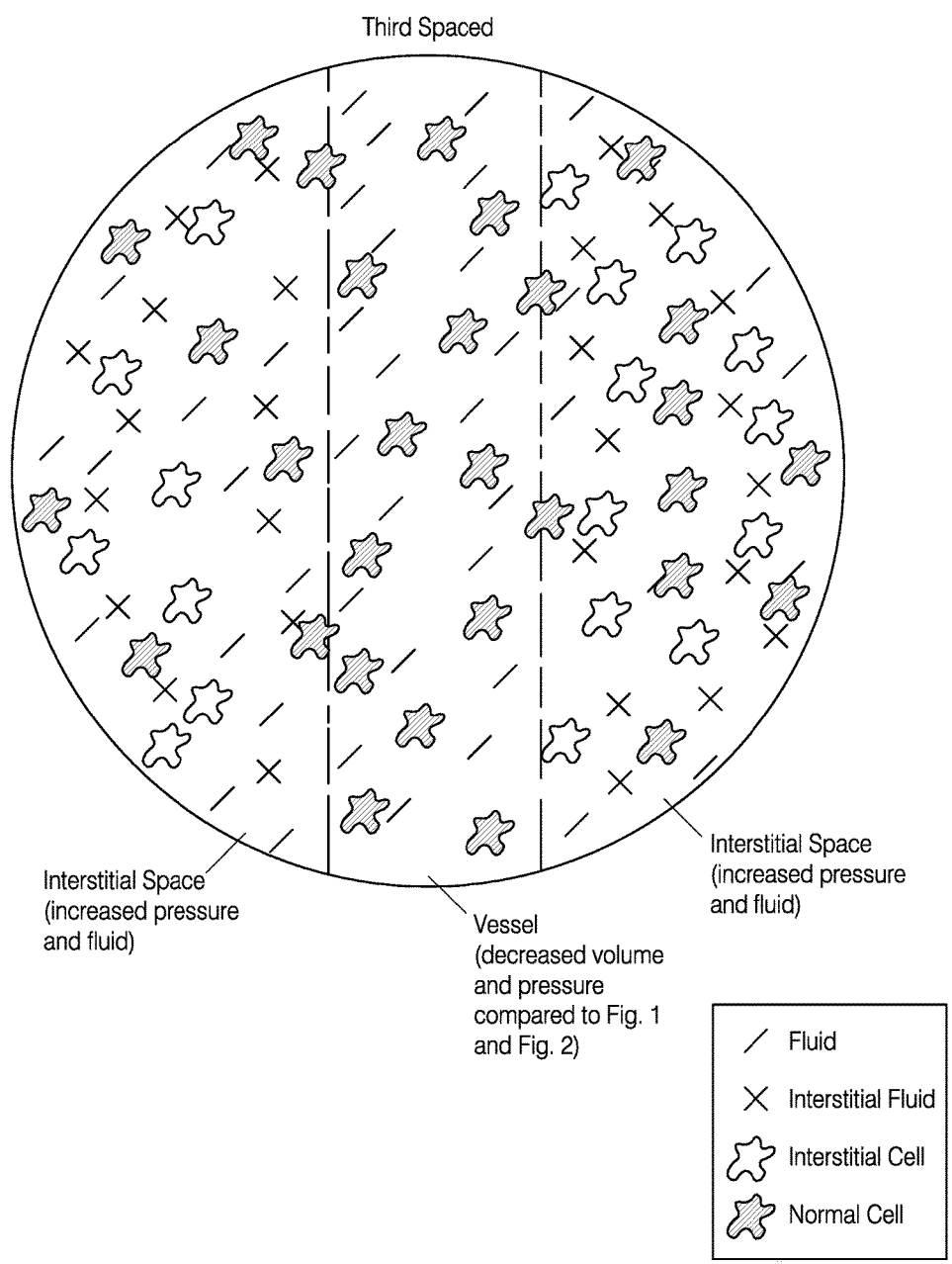
FIG. 3 is a side cross sectional view of a vessel and interstitial fluid and schematic of third spacing.
Figure 4:
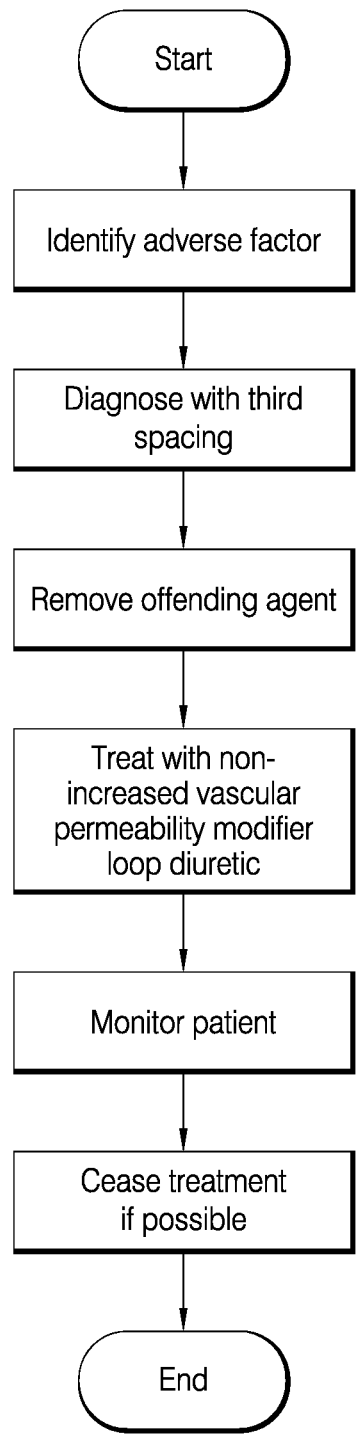
FIG. 4 is a diagram of a method of treatment for third spacing.
Figure 5:
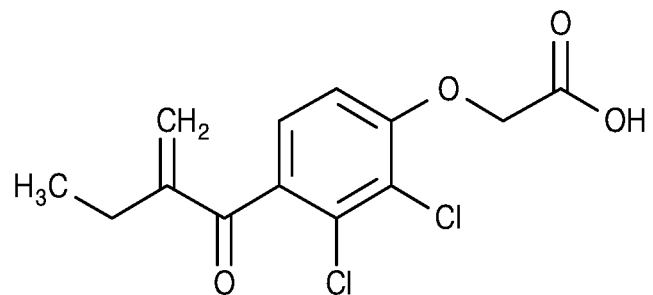
FIG. 5 is a diagram of ethacrynic acid.
Figure 6:
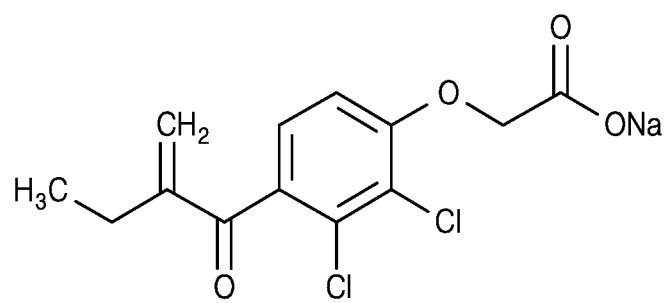
FIG. 6 is a diagram of ethacrynate sodium.

As shown in FIG. 3, third spacing occurs when certain conditions lead to fluid or material sequestration in a third space. For instance, mediators can cause fenestration or leakage of the vessel. This third space is extracellular but is not in equilibrium with either the extracellular fluid (ECF) or the intracellular fluid (ICF). As such, the fluid is effectively lost from the ECF, which can result in hypovolemia as the contents of the vessel egresses into the interstitial space and pressure and volume within the vessel falls. Moreover, third spacing of fluid, materials, or both, on the other hand can include clinically apparent edema and that which is not—however, the two are not the same within the art as described above and demonstrated below.

For example, a blood clot in the left thigh may cause swelling of the left leg, which can result in both intravascular and interstitial fluid increasing until the clot resolves or is removed. Although interstitial fluid is accumulating in the leg, the intravascular volume is likewise increasing, e.g. like a plugged drain. Thus, this is not third spacing, since there is no hypovolemia, or decreased fluid in the blood vessel.

In another instance, when an individual inhales a noxious agent, such as chlorine, the inhalation can cause damage to the lung tissue, parenchyma, but it does not cause intravascular fluid accumulation. It causes third spacing of fluid in the lung parenchyma, which in turn results in hypovolemia. In this case, however, the patient does not show clinical edema; as previously discussed, edema can be hard to determine without a significant amount of fluid or material retention. This is especially true in this case where the patient does not show clinical signs of edema but has signs consistent with third spacing.

In terms of third spacing of materials, this occurs when materials move to a third space. For example, proteins can migrate between vessels if endothelial cells become separated sufficiently as such occurs with leaky gut syndrome or with agents that contribute to increased vessel fenestration. In another example, the proteins solidify after third spacing. Third spacing of materials can also occur during an infection. For instance, an empyema, i.e. pus or white blood cells in a pleural space, is the result of fluid or semi-solid material that moves between gaps in the endothelial cells of a blood vessel and thereafter solidifies.

There are various causes for edema and third space. The difference between the two is their causes and how they are treated. Edema occurs when hydrostatic pressure is elevated with a normal oncotic pressure resulting in material being forced into the adjacent interstitial space. There is little to no egression of large hydrophilic materials from the vessel though. Third space occurs when both hydrostatic and oncotic pressure fall within the vessel as hydrophilic materials move through the fenestrated regions of the endothelial cells into the adjacent interstitial regions. This results in hypovolemia and subsequent hypotension within the vessel. Hypotension in this regard is not static though, it can resolve with a new homeostasis.

An idiosyncratic scenario can occur with the edematous patient who also has third space fluid or materials. Clinically the patient appears edematous and is treated with escalating doses of diuretics with minimal to no change in weight as diuresis contributes to weight loss. Even using combination diuretics in these individuals has minimal gains in their wellbeing and the patient is deemed non-adherent in following medical advice. In reality, greater diuretic treatment has been implemented without substantial improvement in the patient. This method of treatment for clinical edema runs the risk of removing so much fluid intravascularly that the patient is at risk for shock and worsening the case of third space. The mental anguish that results for all parties perpetuates more treatment failures using this approach. An alternative approach with these patients is imperative in resolution of their condition. This approach is discussed in Example 2.

Allergy, Hypersensitivity, and Adverse Reaction:

Much debate has gone into sulfa/sulfonamide allergic reaction, hypersensitivity, and adverse reaction. The range of which can extend from mild to severe depending on various factors.

Allergy:

An allergy has traditionally been known as a Type I Hypersensitivity, and typically involves an Immunoglobulin E (IgE)-mediated immune response which is severe, i.e. anaphylaxis. Healthcare providers are aware of the IgE mediated anaphylactic reaction, Hypersensitivity Type I, and how to treat it. Although specific treatments may vary depending on the cause of the anaphylaxis, most treatments involve Basic Life Support (BLS) or Advanced Cardiac Life Support (ACLS) protocol.

Hypersensitivity:

There are three additional Hypersensitivities Types, referred to as Type II-IV. These lesser known types are just as important as Type I, but are often masked as detailed below or present in a delayed sequence.

Reactions Type II-IV are treated pending their presentation in a patient. Therefore, treatment may be delayed due to the onset of the hypersensitivities presentation, which can take up to three days, such as associated with Type IV presentation, or over a couple of weeks in the case of serum sickness, Type III. Type II reactions can occur more quickly than Type III-IV pending their presentation, such as causing myalgias, hematuria, and anemia with an incompatible ABO blood transfusion for example.

Adverse Reactions:

A final category is adverse reactions, which are less severe but are more common. They can be as simple as upset stomach, which is the most common reaction in this class, to symptoms mimicking more serious reactions listed above. Adverse reactions do not fall within the above classifications of an allergy or hypersensitivity due to mild symptoms or signs associated with the reaction. There are various reasons why findings of an adverse reaction may not be observed.

Given the subtle nature of an adverse reaction, the use of over the counter medications such antihistamines, which block some symptoms, or symptoms that they are so long-standing and mild, a patient may be unaware that they are having an adverse reaction. Case in point, some medications contribute to darkening of the skin over time. As such, it is not apparent until one looks at photos such as a driver's license taken before the medication was started. The importance of identifying and treating adverse reactions cannot be understated, as they are present in many manifestations of DIHS and related syndromes.

When an individual suffers from an allergy, hypersensitivity, or adverse reaction, histamine is released along with other mediators that contribute to return to homeostasis. These mediators result in increased vascular permeability if sufficient amounts are released, this in turn can lead to third spacing. Treatment commonly includes the use of antihistamine, oxygen, epinephrine if warranted, and steroids. Although their use can mean the difference between life and death, they themselves have risks associated with them with short and long term use, especially steroids.

Activation of Complement Cascade:

The above treatment measures do not effectively treat another mechanism of the body's defense against an allergen or other threat to homeostasis. This involves activation of the complement cascade. The complement cascade is an integral aspect of the human body, which helps to maintain homeostasis.

By invoking the complement cascade, several mediators are released which increase fluid retention. This is done through various mechanisms, one of which is increasing vascular permeability contributing to third spacing. The principle mediators of this are complement C3, C4, and C5 and related compounds. Although other non-complement mediators such as histamine, leukotrienes, and prostaglandins play a factor as well; antihistamines, leukotriene blockers and steroids, aspirin and non-steroid anti-inflammatory agents, can modulate their actions respectively.

There are no agents to decrease the C3, C4, and C5 effects other than steroids. Steroids have their deficiencies, however, as steroids cannot be continued indefinitely and have side effects as well, such as elevated blood sugar, infections, and adrenal insufficiency. The extent of the side effects associated with steroids has resulted in the requirement for a prescription, whereas many antihistamines do not. Unlike steroids though, C3, C4, and C5 are not affected by antihistamines. Further antihistamine tolerance develops over time in some patients, which has the drawback of requiring the patient to use alternating effective antihistamines periodically in order to control their symptoms.

Even absent an allergy or hypersensitivity, the complement cascade can be activated thereby triggering vascular permeability, which contributes to third spacing. For instance, individuals showing skin lesion may not necessarily have an allergy or hypersensitivity, but can have an adverse reaction caused by various factors. For example, a sunburn does not necessarily mean an allergy, it simply may indicate overexposure to the sun and resultant damage to the skin. The damage that is caused to the skin, however, results in activation of the complement cascade along with other mediators to restore homeostasis, which in turn causes vascular permeability. In normal individuals this results in transient edema, which resolves in short time without sequela or use of intervention. However, in susceptible individuals such as those who have (idiopathic) polymorphous light eruption (PMLE) and whom may be on medications that are photosensitizers, this not only results in increased vascular permeability but also third spacing. As such, it is more difficult for them to have resolution without some intervention. Other activators of the complement cascade can be environmental factors, such cold as seen with frostbite, heat with burns and related trauma.

Photosensitizers are compounds which can absorb energy, such as light in the form of photons. In doing so, the energy absorbed results in movement of electrons in the compounds to higher orbits, akin to a satellite going into a higher orbit above the earth. These higher orbits are not usually occupied by the electrons, and as such they are unstable. Eventually the electrons try to return to their normal position. To do so, they must release the gained energy that the photon instilled in them. In doing so, the energy is dissipated into the surrounding region—in this case tissue. This can result in damage to the tissue which is not use to this process.

Many sulfa/sulfonamide compounds run the risk of being a photosensitizer and as a result patients need to be aware of exposure to direct sunlight. A tip-off to such occurring is the patient shows an exanthema, for instance, a redness of the skin involving the sun exposed areas, that started shortly after the using the medication. This can occur during summer, as well as winter, caused by direct and indirect sunlight, which is worse at high altitudes due to increased radiation. As time progresses the exanthema can become generalized to non-sun exposed areas of the body. In any event, photosensitizers have the potential to destabilize homeostasis in susceptible individuals.

Current treatments in the art in these situations, such as with sulfa/sulfonamides, can exacerbate these problems, as can other medicaments and treatment methodologies. In these instances, the medications are not causing an allergy, hypersensitivity, or adverse reaction, but rather are contributory factors or side effects of treatment. These forms or treatment are the equivalent of drinking saltwater to quench thirst.

Bradykinin:

Bradykinin also contributes to vascular permeability and thus third spacing, but in a different manner than complement cascade. It is activated via the Hageman factor; this factor is important in activating the clotting system. In this regard when homeostasis is interrupted and the clotting system is triggered, via various medications or environmental factors, bradykinin is released, thus increasing vascular permeability and third spacing. Bradykinin is also thought to be associated with certain medications such as angiotensin converting enzymes (ACEI) as an adverse reaction—a cough in this instance. The mechanism is not exactly known but these medications increase the amount of bradykinin. This apparently is not the case with the use of angiotensin receptor blockers (ARB), which work by blocking the site of angiotensin instead of decreasing its production and thus producing bradykinin. Resolution of the cough has been observed in individuals changed from ACEI to ARB.

Redundancy:

The human body has evolved the ability to use its defenses against insults through redundancy. For example, immunoglobulins bond to infectious bodies, such as bacteria and viruses, to assist in labelling them as foreign. In so doing, this makes it easier to remove the offending agent from the body, by Type I-IV Hypersensitivities, complement cascade, and other mechanisms.

Immunoglobulins have evolved in such a manner that they have variations in their attachment sites that allow flexibility in what attaches to them. To understand this better, think of a lock and a key. To unlock the lock, one must have the right key. In the case of immunoglobulins, multiple different keys (allergens) can open the lock or close and lock it. This is referred to as a redundancy of the immunoglobulin. This redundancy at the binding site can trigger an allergic or hypersensitivity reaction, even though the compounds may not seem to be related, e.g. thiazide verse furosemide. A similar example would include cross reactivity between latex and avocados; although unrelated in terms of their appearance, they have similar proteins. These proteins trigger a hypersensitivity by binding to the epitope as discussed above.

In order for the immune system to react to an allergen, the weight of the offending agent must be at least 1000 Daltons, and some times as large as 6000 Daltons. Most diuretics are not in this range of mass. The large protein albumin, on the other hand, is in excess of this value along with other proteins in the body (e.g. such as on cell walls). Albumin is the primary agent in the body that binds drugs, once they have been administered and absorbed. Albumin also functions in the regulation of intravascular oncotic pressure along with influencing the tonicity of the vessel as previously discussed. The albumin drug complex then travels through the vascular system to the site or sites the complex is intended to function. The drug is then released at that site or sites and starts its action.

Proteins having similar bonding sites as albumin can also bind to drugs, such as cell walls or DNA/RNA inside cells. Upon doing so, the immune system either recognizes the complex as normal or foreign. If the latter occurs, then an allergic or hypersensitivity reaction can occur. Even if the drug is not present in the system, the redundancy of the binding site, also known as the epitope, of the immunoglobulin can bind to the protein to invoke a reaction, based on the redundancy theory. Thus, a DIHS can persist even though the offending agent is no longer present. In this case, the drug starts an autoimmune process, e.g. Drug Induced Lupus Erythematous (DILE), which is a form a DIHS, occurring with Hydralazine in susceptible individuals.

Difficulty in Removal of Offending Agent or Agents:

Although removal of the offending agent in order to alleviate the allergy or hypersensitivity that the patient is suffering from is sought after, it is not always possible. For instance, although the number of medications thought to contribute just to DILE has not changed much in the last sixteen years, it is an extensive list. Furthermore, there is considerable confusion with respect to the various medication names, both generic and trade, such that it is not obvious which of these medications contain a sulfa/sulfonamide group. Thus a patient may inadvertently be unknowingly placed on a different sulfa/sulfonamide compound, which does little, or nothing, other than perpetuate the patient's symptoms or disease through redundancy described previously. As such, healthcare providers face numerous difficulties when trying to institute appropriate care for a patient.

In any case of an allergy or hypersensitivity to a medication, that medication as per the PDR, must be stopped to prevent further harm—unless no other alternative or desensitization can be accomplished. The individual should not be placed back on the offending agent. As the offending agent is stopped, as is the case sulfa/sulfonamide allergies and its derivatives, as well as other medications, excess fluid may have been third spaced. As such, there is a need to address this third spaced fluid.

Outside of pharmacological applications, it is common for people to avoid contact that may cause an allergic, hypersensitivity, or adverse reaction. For example, people with a peanut allergy need to avoid peanuts or their derivatives. Unfortunately this is not always the case. Neurosyphilis requires penicillin as the treatment of choice. In this case, the person requiring penicillin who is allergic to it must be desensitized to it over time. This is done by injecting small amounts of the medication in a controlled environment. Eventually the patient can take the medication without having a reaction. The same is true for immunotherapy; patients can receive in a controlled environment small amounts of the extracts until they do not react, e.g. patients allergic to hymenoptera bees or wasps.

Confusion in Treatment:

In the case of sulfa/sulfonamides, the state of the art is confusing. To an ordinary practitioner, a medication may not be considered as an offending agent unless a patient has a history of anaphylactic reaction. Thus, an ordinary practitioner will conventionally continue treatment with the offending medication even though they may have findings of mild hypersensitivity reactions. In other instances, the mild hypersensitivities or adverse reactions may be entirely masked or partially obscured by other treatments, e.g. antihistamines.

Treatment of Third Spacing:

From the above, there are numerous adverse factors that can lead to third spacing currently in the art. In particular, allergies, hypersensitivities, adverse reactions, and environmental factors that can instigate vascular permeability resulting in third spacing. Additional environmental instigators, such as over exposure to the sun, can instigate the complement cascade and other mediators, which in turn increases vascular permeability and third spacing. Pharmacological treatments can result in adverse reactions such as DIHS, which includes other syndromes such as DILE, Drug Related Eosinophilic Systemic Syndrome (DRESS), and others, can lead to third spacing. The use of medication also generates bradykinin along with other mediators to invoke return to homeostasis. Further, using similar compounds to remove third spaced fluids can contribute to altering the various immunoglobulins, thus contributing to their ability to use redundancy as a means to adapt and again return to homeostasis. This in turn makes more compounds immunogenic.

Furthermore, the current methods of treatment, as described above, fail to acknowledge either intentionally or unintentionally third spacing. For instance, antihistamines fail to block the complement cascade or otherwise mask or mute underlying adverse reactions or hypersensitivities. Additionally, many sulfa/sulfonamide compounds and medications contribute to the allergy, hypersensitivity, or adverse action directly or as a side effect.

These all contribute to the new indication for the use of a non-sulfonamide loop diuretic medicament, and in particular embodiments, ethacrynic acid or ethacrynate sodium, for a new treatment of third spacing in the art.

Indications for ethacrynic acid or ethacrynate sodium, both oral therapy (PO) or intravenous (IV), for short term or long term use vary. These include the following where third spacing fluid, materials or both need to be addressed:

1. Patients at risk for loss of homeostasis (by complement activation, bradykinin, histamine release and their mediators) direct, such as photo-dermatitis, photo-allergy, trauma, PMLE (and it's variants such as idiopathic PMLE), or indirect, caused by medications that are photosensitizers, environmental factors such as sunlight.
2. Drug Induced Hypersensitivity Syndrome.
3. Drug Induced Hypersensitivity Syndrome where sulfa/sulfonamides compounds or combination drugs are a contributing factor and or cannot be used.
4. Preload and or afterload reduction.
5. Adverse reactions presenting as atypical forms of DIHS, e.g. upset stomach, pruritus.
6. Failure of sulfa/sulfonamide (or combination medications using a sulfa/sulfonamide) diuretics or requiring escalating doses for 1-6 listed above.

Dosage of ethacrynic acid can vary. In one embodiment, an Adult is treated with one to two 25 mg scored tablets a day, maximum of up to 200 mg a day using 25 mg increases-time designation pending clinical/laboratory response. The duration of use varies, short or long term pending etiology and correction of the hypersensitivity listed above or if an alternative treatment can be done with less adverse outcome. Since the tablets are scored, it is possible to use half of a tablet which equates to 12.5 mg to achieve the same effect of the higher dose upon identifying the causative instigator of the third spaced fluid retention and removing.

In one embodiment of the method of treatment third spacing, a patient is assessed and an adverse factor is identified. An adverse factor includes, among others, an allergy, a hypersensitivity, a drug-induced hypersensitivity, an adverse reaction, and activation of the complement cascade, bradykinin, or other condition causing an increase in vascular permeability resulting in third spacing. Concurrently or separately, the patient is diagnosed with third spacing of fluid, materials, or both is completed.

If necessary and if possible, cessation or removal of the offending agent that is causing the adverse factor is completed, including the elimination or reduction of the environment condition or medication. The patient is then treated using a non-increased vascular permeability modifier loop diuretic. In particular, a non-sulfonamide loop diuretic medicament, and more particularly ethacrynic acid or ethacrynate sodium. This medicament provides the unique advantage of addressing the adverse factor while not contributing to the underlying sensitivity currently caused by other known methodologies in the art.

After treatment or during treatment, the patient is monitored either through follow up visits or in a hospital setting. Upon identifying that the adverse has been effectively treated, treatment is ceased. When possible, the offending agent is also ceased.

For illustrative purposes only, the Examples below demonstrate the process involved in applying the method. These are examples that demonstrate the concept and in no way limit the scope of applications that are possible with these methods.

Example 1

A patient's asthma, fluid retention, fatigue, weight loss and photo dermatitis improve within one weeks-time of stopping furosemide and replacing it with ethacrynic acid. Further, laboratory studies indicated the same (for example resolution of pyuria). Unfortunately the patient could not continue with the medication due to an adverse reaction to one of the constituents in the trade name compound. A benefit during this time to the patient was less use or even elimination of other medications used to treat their asthma, myalgia, dyspepsia along with other symptoms. In this case it is thought that decreasing the medications for allergies the patient was on may have contributed to the unmasking of an allergy to one of the components in the trade name compound.

Individuals with asthma are of special note concerning sulfa/sulfonamides. Sulfa/sulfonamides in these patients may have an adverse effect and caution should be exercised when using them. The reason why is not exactly known, however, asthmatic patients may have components of auto-immunity. In triggering a reaction in one part of the body (for instance an exanthema caused by photosensitizing agents), asthma may flare as a result of the systemic release of various agents to resume homeostasis, such as bradykinin, complement, and histamine, throughout the body. These along with other mediators are important agents in triggering reactive airway disease.

Example 2

A patient who suffered from a mental impairment but knew they were allergic to sulfa/sulfonamide compounds (their blood pressure fell), had clinical evidence of edema even though the patient was on a potent sulfa/sulfonamide medication. The patient was placed on ethacrynic acid for a short period of time while stopping the sulfa/sulfonamide compound and in one month, 40 pounds of fluid was removed. In this case, the patient not only had clinical evidence of edema, they also had third spacing of fluid refractory to sulfa/sulfonamide they were on. Unfortunately the patient was lost to follow up.

Example 2 demonstrates a clinical scenario where a patient taking sulfa/sulfonamide compounds has clinical edema and third spaced material without hypotension. The situation can be equated to a waterway that has stagnant areas along its path that eventually flow back into the waterway. Based on this depiction, the stagnant areas represent where the third spaced fluid or material is collected and is clinically seen as edema. The oncotic and hydrostatic pressures in these areas increase to a point that they ultimately cannot increase any further. Eventually back flow of fluid or material moves into the fenestrated vessels from where they initially left, setting up a new homeostasis. In this regard, hydrostatic and oncotic pressures normalize in the vessel and are in equilibrium with the interstitial area. Blood pressure normalizes as a result due to hypovolemia in the vessel resolving even though fenestrations still exist.

As such, the patient in this case had third spaced fluids in addition to the clinical edema refractory to the sulfa/sulfonamide they were on. Once the patient's medication is altered to the non-increased vascular permeability modifier loop diuretic, the mediators contributing to the ongoing third spaced fluid or materials are no longer present. Thereafter, the fenestrated vessels begin sealing up, the stagnant areas causing the presence of clinical edema resolve by back flowing into the vessel by diffusion. In doing so, blood pressure is returned to normal, allowing perfusion of the kidneys and subsequent diuresis.

As for the patient stating they had low blood pressure in the past with sulfa/sulfonamides; a sulfa/sulfonamide agent, including non-loop sulfa/sulfonamide diuretic, verse loop-sulfa/sulfonamide diuretic can explain this. In this regard, the patient can have a type I hypersensitivity to the former medication but not the latter. Once placed on the sulfa/sulfonamide loop diuretic, unless low blood pressure occurs again or type I-IV hypersensitivities occur, the medication will be continued. Caution should be exercised with sulfa/sulfonamide loop diuretics due to the potential of cross reactivity with other sulfa/sulfonamides. In this aspect the patient had evidence of third space involvement with no evidence of hypotension. The reason is a new homeostasis occurred as described in the waterway example.

Therefore, a method of treatment for third spacing that improves upon the state of the art, limits the number of medicaments a patient is exposed to, provides the possibility of cessation of treatment or treatments, treats and removes the underlying offending agent, and provides resumption of homeostasis by avoiding activation of bradykinin, complement cascade, histamine, and their mediators outside of the use of steroids and other anti-inflammatory agents has been presented.

From the above discussion, accompanying figures and claims, it will be appreciated that the method of treatment for third spacing offers many advantages over the prior art. It will also be appreciated by those skilled in the art that other modifications could be made without parting from the spirit and scope of the invention and fall within the scope of the claims, and are intended to be covered thereby.

What is claimed is:

1. A method of treatment for third spacing, comprising the steps of:
    identifying an adverse factor in a patient;
    diagnosing the patient with third spacing caused by the adverse factor; and
    treating the patient with a therapeutically effective amount of one of the group consisting of a non-sulfonamide loop diuretic, ethacrynic acid, and ethacrynate sodium.

2. The method of claim 1 further comprising the step of monitoring the patient during the treating step.

3. The method of claim 1 further comprising the step of removing an offending agent causing the adverse factor.

4. The method of claim 1 wherein the patient is diagnosed with the third spacing of fluid.

5. The method of claim 1 wherein the patient is diagnosed with the third spacing of material.

6. The method of claim 1 wherein the patient is diagnosed with the third spacing of fluid and material.

7. The method of claim 1 wherein the adverse factor is Drug Induced Hypersensitivity Syndrome.

8. The method of claim 3 wherein the offending agent is a sulfonamide compound.

9. The method of claim 1 wherein edema is not present in the patient.

10. The method of claim 1 wherein the adverse factor is a drug-induced hypersensitivity is present in the patient.

11. The method of claim 1 wherein the adverse factor is a hypersensitivity is present in the patient.

12. The method of claim 1 wherein the adverse factor is a side effect of a medication.

13. The method of claim 1 wherein the adverse factor is a genetic factor.

14. The method of claim 13 wherein the genetic factor is idiopathic polymorphous light eruption.

15. A method of treatment for third spacing, comprising the steps of:
    identifying an adverse factor in a patient;
    diagnosing the patient with third spacing of a lymphatic vessel caused by the adverse factor; and
    treating the patient with a therapeutically effective amount of one of the group consisting of a non-sulfonamide loop diuretic, ethacrynic acid, and is ethacrynate sodium.

16. The method of claim 15 wherein the adverse factor is caused by a sulfonamide compound.

17. The method of claim 15 wherein the adverse factor is a medication that is a photosensitizer.

18. The method of claim 15 wherein the adverse factor is a medication.

19. The method of claim 15 wherein the adverse factor is a genetic factor.

20. The method of claim 19 wherein the genetic factor is idiopathic polymorphous light eruption.

21. A method of treatment for third spacing, comprising the steps of:
    identifying a side effect in a patient;
    diagnosing the patient with third spacing caused by the side effect; and
    treating the patient with a therapeutically effective amount of one of the group consisting of a non-sulfonamide loop diuretic, ethacrynic acid, and is ethacrynate sodium.

22. The method of claim 21 wherein the side effect is caused by a sulfonamide compound.

23. The method of claim 21 wherein the adverse factor is a medication that is a photosensitizer.

24. The method of claim 21 wherein the side effect exacerbates a genetic factor.

25. The method of claim 24 wherein the genetic factor is idiopathic polymorphous light eruption.

* * * * *